United States Patent
Chen et al.

(10) Patent No.: US 10,076,310 B2
(45) Date of Patent: Sep. 18, 2018

(54) METHOD AND DEVICE FOR DETECTING OCCLUSION/REOPENING OF AN ARTERY AND SYSTEM FOR MEASURING SYSTOLIC BLOOD PRESSURE

(75) Inventors: Yinan Chen, Shanghai (CN); Weijia Lu, Shanghai (CN); Jianyi Zhong, Hangzhou (CN); Ajay Anand, Fishkill, NY (US); John Petruzzello, Carmel, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 721 days.

(21) Appl. No.: 14/234,449

(22) PCT Filed: Jul. 17, 2012

(86) PCT No.: PCT/IB2012/053640
§ 371 (c)(1),
(2), (4) Date: Jan. 23, 2014

(87) PCT Pub. No.: WO2013/014575
PCT Pub. Date: Jan. 31, 2013

(65) Prior Publication Data
US 2014/0180114 A1    Jun. 26, 2014

(30) Foreign Application Priority Data

Jul. 28, 2011 (WO) ................ PCT/CN2011/077752

(51) Int. Cl.
*A61B 8/06* (2006.01)
*A61B 8/08* (2006.01)
(Continued)

(52) U.S. Cl.
CPC ............ *A61B 8/5223* (2013.01); *A61B 5/022* (2013.01); *A61B 8/04* (2013.01); *A61B 8/06* (2013.01);
(Continued)

(58) Field of Classification Search
CPC ........... A61B 5/021; A61B 5/026; A61B 8/00; A61B 8/04; A61B 8/06
See application file for complete search history.

(56) References Cited

U.S. PATENT DOCUMENTS 4,205,688 A    6/1980 Hauser et al.
4,625,277 A    11/1986 Pearce et al.
(Continued)

FOREIGN PATENT DOCUMENTS

JP    H1080342       3/1998
WO    2010/063976    6/2010
WO    2010061197 A1  6/2010

*Primary Examiner* — Rochelle Turchen

(57) ABSTRACT

An occlusion and/or reopening of an artery of a body caused by a changing pressure applied on the artery is detected. The systolic blood pressure of an artery of a body is also measured. A Doppler Ultrasound transducer attached to the exterior of the body outputs a blood flow signal indicative of a change of the blood flow in the artery caused by the changing pressure. At least one variable of a first variable indicative of the magnitude of the blood flow and a second variable indicative of the periodicity of the blood flow is derived from the blood flow signal. The occlusion and/or reopening of the artery is detected on the basis of the at least one variable. In this way, the occlusion/reopening of the artery can be detected automatically. Since the need to manually detect the occlusion and reopening of the artery by listening with a stethoscope or a Doppler probe is eliminated, the detecting result is more predictable and repeatable, and therefore also more accurate.

18 Claims, 2 Drawing Sheets

(51) Int. Cl.
*A61B 8/04* (2006.01)
*A61B 5/022* (2006.01)
*A61B 8/00* (2006.01)
*A61B 5/00* (2006.01)

(52) U.S. Cl.
CPC ............ *A61B 8/4483* (2013.01); *A61B 8/488* (2013.01); *A61B 5/6824* (2013.01)

(56) References Cited

U.S. PATENT DOCUMENTS

| | | |
|---|---|---|
| 5,072,736 A | 12/1991 | Ogawa et al. |
| 6,171,254 B1 | 1/2001 | Skelton |
| 2008/0119743 A1 | 5/2008 | Friedman et al. |
| 2010/0106016 A1 | 4/2010 | Orbay et al. |
| 2010/0292586 A1 | 11/2010 | Rooke et al. |

METHOD AND DEVICE FOR DETECTING OCCLUSION/REOPENING OF AN ARTERY AND SYSTEM FOR MEASURING SYSTOLIC BLOOD PRESSURE

FIELD OF THE INVENTION

The invention relates to non-invasive blood pressure measurement, in particular to a method and a device for detecting occlusion/reopening of an artery and a system for measuring systolic blood pressure (SBP).

BACKGROUND OF THE INVENTION

Unlike invasive blood pressure measurement, non-invasive blood pressure measurement is an indirect method of measuring the blood pressure in an artery of the human body. Currently, there are two categories of non-invasive blood pressure measurement methods.

One method is the auscultatory method (from the Latin word for "listening"), which is the predominant method of clinical measurement due to its accuracy. According to the auscultatory method, an inflatable cuff of a sphygmomanometer is used to apply a changing pressure on an artery to restrict blood flow in the artery. The cuff is first inflated until the artery is completely occluded and then deflated until the artery is open again. The pressure values at the moment of occlusion and at the moment of reopening are commonly called SBP-I (SBP during inflation) and SBP-D (SBP during deflation), respectively. Clinicians manually detect the moment of occlusion and the moment of reopening of the artery by listening with a stethoscope or a Doppler probe and read the SBP values from the sphygmomanometer. The clinicians should have no hearing deficit and are required to highly focus on the devices during the whole measuring procedure. Consequently, when using the auscultatory method to measure SBP, the clinicians might easily start to feel tired, as a result of which the accuracy of the detected moments of occlusion and reopening of the artery is impacted accordingly.

The other method is the oscillometric method. Existing automatic blood pressure measuring devices are all based on the oscillometric method. Clinicians enjoy the convenience brought by the oscillometric method. However, in comparison with the auscultatory method, the oscillometric method is relatively inaccurate, because the measurements are calculated based on statistics without respect to individuals.

Thus, existing blood pressure measurement methods are either inconvenient to use or inaccurate.

SUMMARY OF THE INVENTION

Based on the understanding of the technical problems and prior art described above, it would be desirable to automatically detect the moment of occlusion and/or reopening of an artery without any intervention from clinicians. It would also be desirable to automatically measure SBP while still achieving good measurement accuracy.

To better address one or more of the above concerns, according to an embodiment of an aspect of the present invention, a method of detecting occlusion and/or reopening of an artery of the body caused by a changing pressure applied on the artery is provided. The method comprises the steps of:

obtaining, using a Doppler Ultrasound transducer attached to the exterior of the body, a blood flow signal indicative of a change of the blood flow in the artery caused by the changing pressure;

deriving, from the blood flow signal, at least one of a first variable indicative of the magnitude of the blood flow and a second variable indicative of the periodicity of the blood flow;

detecting the occlusion and/or reopening of the artery on the basis of the at least one variable.

The basic idea is to detect the occlusion/reopening of an artery on the basis of at least one of a first variable indicative of the magnitude of the blood flow in the artery and a second variable indicative of the periodicity of the blood flow in the artery. In other words, the occlusion/reopening of the artery is automatically detected on the basis of the change of the amplitude and/or the periodicity of the blood flow in the artery. Furthermore, the variables are derived from a blood flow signal, and the blood flow signal refers to any signal indicative of a change of the blood flow in the artery and is obtained using a Doppler Ultrasound transducer.

In this way, the occlusion/reopening of the artery can be detected automatically. Since the need to manually detect the occlusion and reopening of the artery by listening with a stethoscope or a Doppler probe is eliminated, the detecting result is more predictable and repeatable, and therefore also more accurate. Furthermore, since the detecting procedure is automated, the occlusion and reopening of the artery can be detected more conveniently.

In an embodiment, the occlusion is detected when the first variable is less than a first threshold and/or the second variable is outside a first range; and the reopening is detected when the first variable is greater than a second threshold and/or the second variable is within a second range.

When the first variable is less than the first threshold and thus indicates that the magnitude of the blood flow is sufficiently low, the blood flow in the artery can be determined to have disappeared and the artery can, accordingly, be determined as being occluded. When the second variable is out of the first range and thus indicates that the periodicity of the blood flow is out of the first range, the blood flow in the artery can be determined as having disappeared and the artery can be determined as being occluded. This can be ascribed to the fact that, when the blood flow is not occluded, the periodicity of the blood flow is in synchronism with the heart rate and is generally within a certain range. Thus, the occlusion is detected when the first variable is less than the first threshold and/or the second variable is out of the first range. Similarly, the reopening of the artery is detected when the first variable is greater than the second threshold and/or the second variable is within the second range.

In another embodiment, the reopening of the artery is detected when the first variable is greater than a second threshold and/or the second variable is within a second range for a predefined time period.

When, for the predefined time period, the first variable indicates that the amplitude of the blood flow remains greater than the second threshold and/or the second variable indicates the periodicity of the blood flow remains within the second range, this means that the blood flow not only re-appears but also that it is becoming stable and, thus, that the artery is completely reopened. In this way, the reopening of the artery can be detected more reliably and more accurately. For example, when the artery starts to reopen, the blood flow could re-appear for a while and then disappear again, which is called Gap phenomenon, and only when the artery is completely reopened, the re-appearance of the blood flow becomes stable. According to this embodiment, since the reopening of the artery is detected when the blood flow becomes stable, the possibility of false detection caused by the Gap phenomenon can be reduced.

In another embodiment, the method further comprises the step of determining at least one of the first threshold, the first range, the second threshold and the second range from the blood flow signal.

Both the magnitude and the periodicity of the blood flow vary for different individuals. For example, the magnitude of the blood flow for an adult is generally higher than for a child, and the periodicity of the blood flow corresponding to the heart rate is relatively low for an athlete. Thus, instead of predefining a uniform threshold or range for all individuals, the first threshold, the first range, the second threshold and the second range can be determined for each individual from the blood flow signal of the individual, such that the occlusion and/or reopening of the artery can be detected more reliably and more accurately.

In another embodiment, in the deriving step, at least one of a value of the first variable and a value of the second variable for a time window is calculated from the blood flow signal in the time window; and in the detecting step, the occlusion and/or reopening of the artery in the time window is detected on the basis of the at least one value for the time window.

As the changing pressure changes over time, at least one of a value of the first variable and a value of the second variable for a current time window is calculated from the blood flow signal in the current time window so as to indicate the current magnitude and/or the current periodicity of the blood flow. When the at least one value indicates that the artery is occluded and/or reopened, it can be determined that the artery is occluded and/or reopened in the current time window.

In another embodiment, the method further comprises the step of determining a maximum value of the changing pressure according to the detected occlusion of the artery.

In this way, the maximum value of the changing pressure can be automatically determined. Moreover, since the maximum value of the changing pressure is not constant, but is adjusted to the actual condition of the artery, it is ensured that the pressure is sufficient for the occurrence of the occlusion, while any damage to the artery due to an excessively high pressure is prevented.

According to an embodiment of another aspect of the present invention, a device for detecting occlusion and/or reopening of an artery of the body caused by a changing pressure applied on the artery is provided. The device comprises:
  an obtaining unit for obtaining a blood flow signal indicative of a change of a blood flow in the artery caused by the changing pressure using a Doppler Ultrasound transducer attached to the exterior of the body;
  a deriving unit for deriving, from the blood flow signal, at least one of a first variable indicative of the magnitude of the blood flow and a second variable indicative of the periodicity of the blood flow;
  a detecting unit for detecting the occlusion and/or reopening of the artery on the basis of the at least one variable.

According to an embodiment of yet another aspect of the present invention, a system for measuring the systolic blood pressure of an artery of the body is provided. The system comprises:
  an inflatable cuff attachable to the exterior of the body for applying a changing pressure on the artery;
  a pressure sensor for obtaining a plurality of pressure values of the changing pressure at a plurality of time points;
  a detecting device for detecting occlusion and/or reopening of the artery of the body caused by the changing pressure applied on the artery as described in the above;
  a determining device for determining the systolic blood pressure from at least one of a first pressure value of the changing pressure at a time point corresponding to the detected occlusion of the artery, and a second pressure value of the changing pressure at a time point corresponding to the detected reopening of the artery.

By means of such a system, the systolic blood pressure of an artery can be measured automatically. Since the need to manually detect the occlusion and reopening of the artery by listening with a stethoscope or a Doppler probe is eliminated and the need to manually read the pressure value at the time when occlusion and/or reopening of the artery occurs is also eliminated, the measuring result is more predictable and repeatable, and therefore also more accurate. Furthermore, since the measuring procedure is automated, the systolic blood pressure can be measured more conveniently.

Further, the first pressure value and the second pressure value correspond to the SBP-I and the SBP-D, respectively, and the systolic blood pressure is determined from either SBP-I or SBP-D or both.

In another embodiment, the detecting device is configured to determine a time point for decreasing the changing pressure according to the detected occlusion of the artery; and the inflatable cuff is configured to start deflating at the determined time point.

In this way, the inflatable cuff is controlled automatically and accurately.

These and other aspects of the invention will be apparent from and elucidated with reference to the embodiments described hereinafter.

DESCRIPTION OF THE DRAWINGS

The above and other objects and features of the present invention will become more apparent from the following detailed description considered in connection with the accompanying drawings, in which.

The same reference numerals are used to denote similar parts throughout the figures.

DETAILED DESCRIPTION

A detailed description of the present invention is given below in connection with the accompanying drawings.

Figure 1:
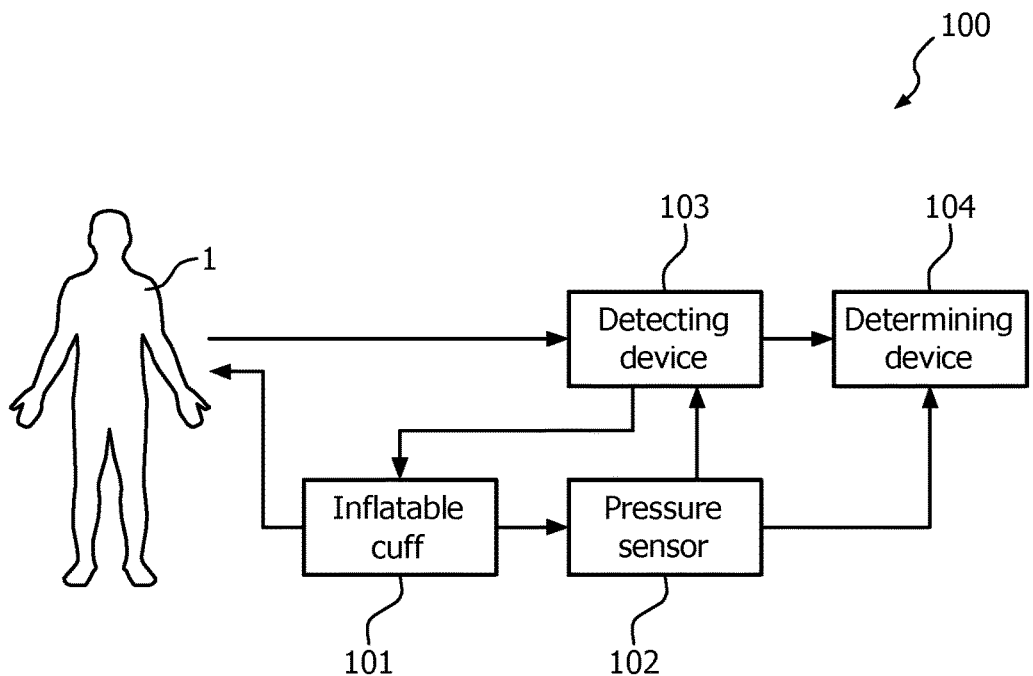
FIG. 1 depicts a schematic diagram of a system for measuring the systolic blood pressure of an artery in accordance with an embodiment of the present invention.

FIG. 1 depicts a schematic diagram of a system for measuring the systolic blood pressure of an artery in accordance with an embodiment of the present invention.

Referring to FIG. 1, the system 100 comprises an inflatable cuff 101, a pressure sensor 102, a detecting device 103 and a determining device 104.

The inflatable cuff 101 is intended to be attached to the exterior of the body 1 to apply a changing pressure on an artery of the body 1. For example, the inflatable cuff 101 can be wrapped around the upper limb of the body to apply the changing pressure on the brachial artery. For another example, the inflatable cuff 101 can be wrapped around the lower limb of the body to apply the changing pressure on the posterior tibial artery and/or dorsalis pedis artery.

The pressure sensor 102 is configured to obtain values of the changing pressure applied by the inflatable cuff. In particular, the pressure sensor 102 obtains a plurality of pressure values of the changing pressure at a plurality of time points.

The detecting device 103 is configured to detect occlusion and/or reopening of an artery of the body caused by the changing pressure applied on the artery. As is well-known, the artery is occluded when the applied pressure is sufficiently high, and the artery is reopened when the applied pressure decreases below a certain value. Accordingly, during the increase of the changing pressure, the detecting device 103 detects when occlusion of the artery occurs; and during the decrease of the changing pressure, the detecting device 103 detects when the artery is reopened.

The determining device 104 is configured to determine the systolic blood pressure from at least one of a first pressure value of the changing pressure at a time point corresponding to the detected occlusion of the artery, and a second pressure value of the changing pressure at a time point corresponding to the detected reopening of the artery. As is well-known, the systolic blood pressure (SBP) comprises SBP-I and SBP-D, wherein SBP-I is the pressure applied by the cuff 102 at a time when the artery is occluded during the inflation of the cuff 102, and SBP-D is the pressure applied by the cuff 102 when the artery is reopened during the deflation of the cuff 102. Thus, the first pressure value and the second pressure value are the SBP-I value and the SBP-D value, respectively.

When only one of the first and the second pressure values is available, the available one is determined to be the systolic blood pressure. When both the first and the second pressure values are available, the determining device 104 can determine the systolic blood pressure in different ways. For example, the systolic blood pressure can be determined as one of the first pressure value and the second pressure value. For another example, the systolic blood pressure can be determined to be the higher one of the first pressure value and the second pressure value.

The determining device 104 can obtain at least one of the first and the second pressure values in different ways. In an embodiment, the pressure sensor 102 provides a plurality of pressure values at the plurality of time points to the detecting device 103, and then the detecting device 103 provides at least one of the first and the second pressure values corresponding respectively to the detected occlusion and reopening of the artery to the determining device 104. In another embodiment, the pressure sensor 102 provides a plurality of pressure values at the plurality of time points to the determining device 104, the detecting device 103 provides at least one of two time points corresponding to the detected occlusion and reopening of the artery to the determining device 104, and then the determining device 104 selects at least one of the first and the second pressure values among the plurality of pressure values from the pressure sensor 102 according to at least one of two time points from the detecting device 103.

Figure 2:
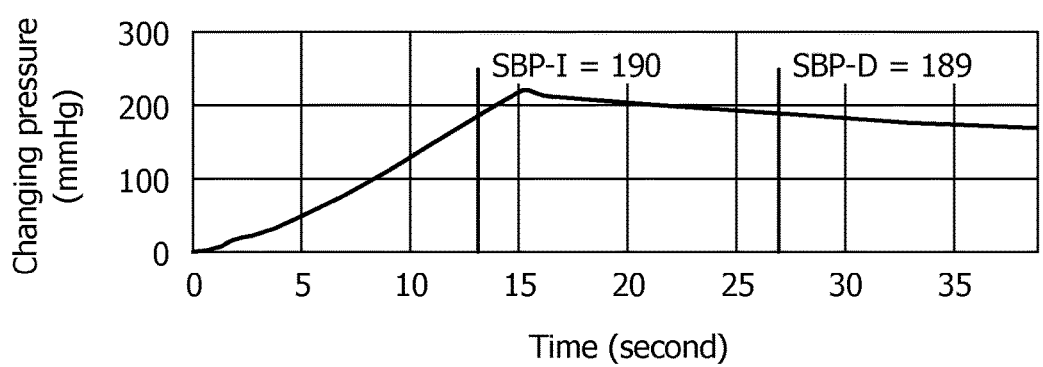
FIG. 2 depicts a diagram of a changing pressure in accordance with an embodiment of the present invention.

FIG. 2 depicts a diagram of a changing pressure in accordance with an embodiment of the present invention. FIG. 2 illustrates a change of the changing pressure versus time.

Referring to FIG. 2, according to an embodiment of the present invention, the changing pressure increases gradually to a maximum pressure value that is sufficiently high for the artery to be occluded, and then starts to decrease to enable the artery to reopen. The pressure values corresponding respectively to the occlusion and the reopening of the artery are denoted as SBP-I and SBP-D.

The maximum pressure value can be set in different ways.

In an embodiment, the maximum pressure value can be predefined. Alternatively, different maximum pressure values can be individually set for different persons. For example, the maximum pressure value is set to be relatively high for a patient with hypertension.

In another embodiment, when the occlusion of the artery is detected in real-time, the maximum pressure value can be adaptively defined according to the detected occlusion. For example, the maximum pressure value is set to be in a range of 20 mmHg to 30 mmHg above the SBP-I value. As shown in the FIG. 2, as the changing pressure increases, the occlusion is detected to occur at about second 13 and the corresponding SBP-I is 190 mmHg. Accordingly, the maximum pressure value is set to, for example, 220 mmHg, and the changing pressure starts to decrease when it reaches the maximum pressure at about second 15. Referring to FIG. 1, the detecting device 103 provides a real-time feedback to the inflatable cuff 101 such that the inflatable cuff 101 can start to decrease the changing pressure according to the detected occlusion of the artery.

Figure 3:
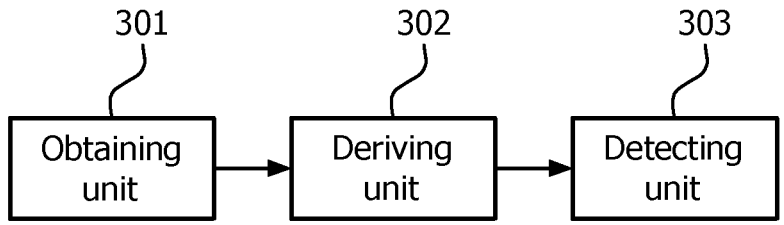
FIG. 3 depicts a schematic diagram of a device for detecting occlusion and/or reopening of an artery in accordance with an embodiment of the present invention.
Figure 4:
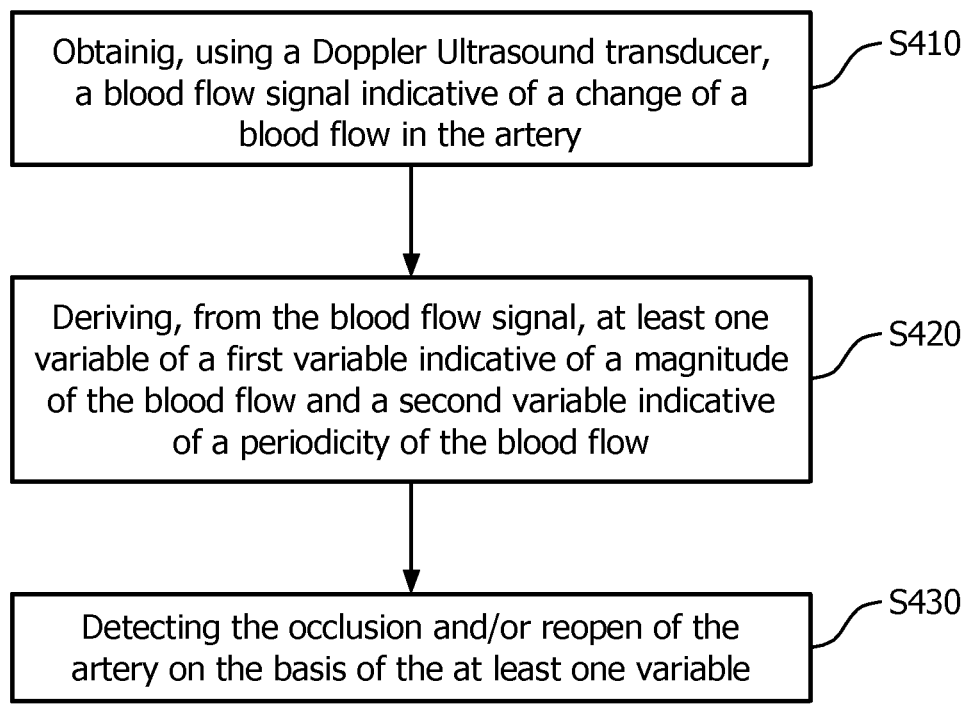
FIG. 4 depicts a flow chart of a method of detecting occlusion and/or reopening of an artery in accordance with an embodiment of the present invention.

FIG. 3 depicts a schematic diagram of a device for detecting occlusion and/or reopening of an artery in accordance with an embodiment of the present invention. FIG. 4 depicts a flow chart of a method of detecting occlusion and/or reopening of an artery in accordance with an embodiment of the present invention.

Referring to FIG. 3, the device for detecting occlusion and/or reopening of an artery, such as the detecting device 103 of FIG. 1, comprises an obtaining unit 301, a deriving unit 302 and a detecting unit 303.

Referring to FIG. 3 and FIG. 4, the method comprises a step S410, in which the obtaining unit 301 obtains a blood flow signal using a Doppler Ultrasound transducer. The blood flow signal indicates a change of a blood flow in the artery.

As is well-known, the Doppler ultrasound transducer can be used to assess direction and velocity of blood flow. The Doppler Ultrasound transducer is attached to the exterior of the body. In particular, the Doppler Ultrasound transducer is attached above the artery. The Doppler ultrasound transducer generates high frequency sound waves and receives echoes from the blood flow in the artery. The echoes are evaluated to determine the direction and the velocity of the blood flow by employing Doppler effect. The Doppler Ultrasound transducer can be a continuous wave Doppler Ultrasound transducer or a pulsed wave Doppler ultrasound transducer.

The blood flow signal can be any kind of signal indicative of the change of the blood flow in the artery. In an embodiment, the blood flow signal refers to the so-called raw acoustic signal obtained using the Doppler Ultrasound transducer. The so-called raw acoustic signal represents the Doppler effect of the echoes, wherein each frequency component is associated with a particular Doppler shift and the amplitude of each frequency component is associated with the amount of blood moving at a velocity corresponding to the particular Doppler shift.

Referring to FIG. 3 and FIG. 4, the method further comprises a step S420, in which the deriving unit 302 derives, from the blood flow signal, at least one of a first variable and a second variable. The first variable indicates the magnitude of the blood flow, and the second variable indicates the periodicity of the blood flow.

According to an embodiment, a predefined time window slides along the time axis, and a value of each of the first and the second variables is calculated for each time window. For example, the time window can be defined as having a width of 3 seconds and sliding for 1 second each time; accordingly, the value of each of the first and the second variables is calculated every second.

The values of the first and the second variables for a given time window can be calculated in different ways. An approach based on time-frequency analysis is described below.

First, a spectrogram of the so-called raw acoustic signal in the given time window is calculated. A spectrogram is a time-varying spectral representation that shows how the spectral density of a signal varies with time, also known as sonagram. Generally, the spectrogram is a graph with a time axis, a frequency axis and a third axis indicating the amplitude at a particular frequency and a particular time. In an embodiment, short-term Fourier transform (STFT) is performed on the raw acoustic signal, and the magnitude squared of the STFT yields the spectrogram. Alternatively, the spectrogram can be also calculated using other known methods such as wavelet transform.

Next, the spectrogram is filtered to remove spectrum components in predefined frequency ranges. For example, the predefined frequency ranges comprises 0-100 Hz and above 3000 Hz.

Next, the amplitude of the filtered spectrogram is accumulated along the frequency axis to obtain a waveform as a function of time, referred to as blood flow waveform hereinafter. Alternatively, the blood flow waveform can be extracted from the filtered spectrogram by extracting the maximum amplitude value along the frequency axis, namely the value of the blood flow waveform is the maximum amplitude value of the filtered spectrogram among all frequencies.

Next, the values of the first and the second variable for the given time window are derived from the obtained blood flow waveform. The value of the first variable is associated with the peak amplitude of the blood flow waveform, and for example, it can be the maximum value or the average value of the peak values in the blood flow waveform. The value of the second variable is associated with the periodicity of the blood flow waveform, and, for example, can be the number of peaks per second. Various methods are known to determine the peak values and the number of peaks and will not be further discussed herein.

Consequently, the values of the first and the second variables for a given time window are calculated from the blood flow signal in the given time window.

Referring to FIG. 3 and FIG. 4, the method further comprises a step S430, in which the detecting unit 303 detects the occlusion and/or reopening of the artery on the basis of the at least one variable of the first variable and the second variable.

In an embodiment, for a given time window, the artery is detected as being occluded in the given time window when the calculated value of the first variable for the given time window is less than the first threshold and/or the calculated value of the second variable for the given time window is out of the first range.

The first threshold and the first range can be determined in different ways. Each of the first threshold and the first range can be constant and predetermined according to statistical data. Alternatively, each of the first threshold and the first range can be determined from the blood flow signal and can therefore vary. For example, the first threshold can be related to noise in the blood flow signal, and the noise can be calculated from the filtered spectrogram. Alternatively, the first threshold can be related to the average peak value in the blood flow waveform, and for example, be set to 10% to 20% of the average peak value. For example, the first range can be determined according to the mean and the standard deviation of the second variable in the previous time windows. Denoting the mean and the standard deviation by $\mu$ and $\sigma$, the first range can, for example, be determined as a range $[\mu-\sigma, \mu+\sigma]$.

Further, for a given time window, the artery is detected as being reopened in the given time window when the calculated value of the first variable for the given time window is greater than a second threshold and/or the calculated value of the second variable for the given time window is outside a second range. The second threshold and the second range can be identical to, respectively, the first threshold and the first range. When the first threshold and the first range are not constant but updated in each time window till the occlusion of the artery, the second threshold and the second range can be set to the latest values of the first threshold and the first range, respectively.

Additionally, when the artery is detected as being reopened in the given time window, the reopening can be further determined as occurring at a time corresponding to the first peak that is greater than the second threshold.

In another embodiment, when the first variable is greater than a second threshold and/or the second variable is within a second range for a predefined time period, the reopening is detected. Preferably, the predefined time period is sufficiently long to contain at least five cycles of the blood flow.

In particular, when the calculated value of the first variable for the current time window is greater than the second threshold and/or the calculated value of the second variable for the current time window is within the second range, the current time window is marked. Then, in a predefined number of subsequent time windows, it is determined whether, for each of the subsequent time windows, the calculated value of the first variable is greater than the second threshold and/or the calculated value of the second variable for the current time window is within the second range. If yes, this indicates that the blood flow is stable, and the artery is determined as being actually reopened in the marked time window. In this way, the possibility of false detection due to the so-called Gap phenomenon can be reduced, and the detected reopening of the artery is therefore more reliable.

As already mentioned in the above, the maximum pressure value of the changing pressure can be adaptively defined according to the detected occlusion of the artery. To do so, it is necessary to detect the occlusion of the artery in real-time. Accordingly, steps S410 to S430 are performed sequentially for each time window. That is to say, once the obtaining unit 310 obtains the blood flow signal in the current time window in step S410, steps S420 and S430 are performed to detect whether the artery is occluded or reopened in the current time window.

It should be noted that the above-mentioned embodiments illustrate rather than limit the invention and that those skilled in the art will be able to design alternative embodiments without departing from the scope of the appended claims. The embodiments are illustrative rather than restrictive. It is intended that the invention include all modifications and variations to the illustrated and described embodiments within the scope and spirit of the invention. In the claims, any reference signs placed between parentheses shall not be construed as limiting the claim. The word "comprising" does not exclude the presence of elements or steps not listed in a claim or in the description. The word "a" or "an" preceding an element does not exclude the presence of a plurality of such elements. In the device claims enumerating several units, several of these units can be embodied by one and the same item of hardware or software. The usage of the words first, second and third, et cetera, does not indicate any ordering. These words are to be interpreted as names.

The invention claimed is:

1. A method of detecting occlusion or reopening of an artery of a body caused by a changing pressure applied to the artery, the method comprising the steps of:
    obtaining a blood flow signal indicative of a change of a blood flow in the artery caused by the changing pressure using a Doppler Ultrasound transducer attached to the exterior of the body;
    deriving, from the blood flow signal, a first variable indicative of a magnitude of the blood flow and a second variable indicative of a periodicity of the blood flow; and
    detecting the occlusion or reopening of the artery on the basis of the magnitude of the first variable relative to at least one magnitude threshold and the periodicity of the second variable relative to a periodicity range.

2. The method as claimed in claim 1, wherein, in the detecting step:
    the occlusion is detected when the first variable is less than a first magnitude threshold and the second variable is outside a first periodicity range; and
    the reopening is detected when the first variable is greater than a second magnitude threshold and the second variable is within a second periodicity range.

3. The method as claimed in claim 2, wherein, in the detecting step:
    the reopening is detected when the first variable is greater than the second magnitude threshold and the second variable is within the second periodicity range in each of a predefined number of subsequent time windows.

4. The method as claimed in claim 2, further comprising the step of:
    determining at least one of the first magnitude threshold, the first periodicity range, the second magnitude threshold and the second periodicity range from the blood flow signal.

5. The method as claimed in claim 1, wherein
    in the deriving step, a value of the first variable and a value of the second variable for a time window is calculated on the basis of the blood flow signal associated with the time window; and
    in the detecting step, the occlusion or reopening of the artery in the time window is detected on the basis of the value of the first and second variable associated with the time window.

6. The method as claimed in claim 1, further comprising:
    the step of determining a maximum value of the changing pressure according to the detected occlusion of the artery.

7. A device for detecting occlusion or reopening of an artery of a body caused by a changing pressure applied to the artery, comprising:
    a Doppler Ultrasound transducer configured to be attached to an exterior of the body and to obtain a blood flow signal indicative of a change of the blood flow in the artery caused by the changing pressure;
    one or more processors configured to:
        derive, from the blood flow signal, a first variable indicative of a magnitude of the blood flow and a second variable indicative of a periodicity of the blood flow; and
        detect the occlusion and/or reopening of the artery on the basis of the magnitude of the first variable and a periodicity of the second variable.

8. The device as claimed in claim 7, wherein:
    the one or more processors are further configured to:
        detect the occlusion when the magnitude of the first variable is less than a first threshold and the periodicity of the second variable is outside a first range; and
        detect the reopening when the magnitude of the first variable is greater than a second threshold and the periodicity of the second variable is within a second range.

9. The device as claimed in claim 7, wherein:
    the one or more processors are further configured to:
    detect the reopening when the first variable is greater than a second threshold and/or the second variable is within a second range in each of a predefined number of subsequent time windows.

10. The device as claimed in claim 8, wherein the one or more processors are further configured to:
    determine at least one of the first threshold, the first range, the second threshold and the second range from the blood flow signal.

11. The device as claimed in claim 7, wherein the one or more processors are further configured to:
    calculate a value of the first variable and a value of the second variable associated with a time window from the blood flow signal in the time window; and
    detect the occlusion or reopening of the artery in the time window on the basis of the value of the first and second variable associating with the time window.

12. The device as claimed in claim 7, wherein the one or more processors are further configured to:
    determine a maximum value of the changing pressure according to the detected occlusion of the artery.

13. A system for measuring the blood pressure of an artery of a body, comprising:
    an inflatable cuff configured to be attached to an exterior of the body for applying a changing pressure on the artery;
    a pressure sensor configured to obtain a plurality of pressure values of the changing pressure at a plurality of time points;
    a Doppler Ultrasound transducer configured to be attached to an exterior of the body and output a blood flow signal indicative of a change of the blood flow in the artery caused by the changing pressure;
    one or more processors configured to:
        receive the blood flow signal,
        derive, from the blood flow signal, a first variable indicative of a magnitude of the blood flow and a second variable indicative of a periodicity of the blood flow, detect the occlusion and/or reopening of the artery on the basis of the magnitude of the first variable and the periodicity of the second variable, determine the blood pressure from at least one of a first pressure value of the changing pressure at a time point corresponding to the detected occlusion of the artery and a second pressure value of the changing pressure at a time point corresponding to the detected reopening of the artery.

14. The system as claimed in claim 13, wherein the one or more processors are further configured to:

determine a maximum value of the changing pressure according to the detected occlusion of the artery; and wherein the inflatable cuff is configured to start deflating when the changing pressure reaches the determined maximum value.

15. The system as claimed in claim 13, wherein the one or more processors are further configured to:

detect the occlusion when the magnitude of the first variable is less than a first threshold and the periodicity of the second variable is outside a first range; and detect the reopening when the magnitude of the first variable is greater than a second threshold and the periodicity of the second variable is within a second range.

16. The system as claimed in claim 13, wherein the one or more processors are further configured to:

detect the reopening when the first variable is greater than a second threshold and/or the second variable is within a second range in each of a predetermined number of subsequent time windows.

17. The system as claimed in claim 15, wherein the one or more processors are further configured to:

determine at least one of the first threshold, the first range, the second threshold and the second range from the blood flow signal.

18. The system as claimed in claim 13, wherein the one or more processors are further configured to:

calculate a value of the first variable and a value of the second variable associated with a time window from the blood flow signal in the time window; and detect the occlusion or reopening of the artery in the time window on the basis of the value of the first and second variable associated with the time window.

* * * * *